US00PP35371P2

(12) United States Plant Patent
Van Swieten

(10) Patent No.: US PP35,371 P2
(45) Date of Patent: Sep. 5, 2023

(54) ***PHALAENOPSIS* ORCHID PLANT NAMED 'PHA858376'**

(50) Latin Name: ***Phalaenopsis* hybrid**
Varietal Denomination: PHA858376

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,001

(22) Filed: Feb. 23, 2023

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHA858376', particularly characterized by having light reddish-purple flowers with reddish-purple stripes, white edges, and reddish-purple lips, flowers that are flat in lateral view, and medium curvature of lateral lobe of lips, and is propagated by meristem tissue culture, is disclosed.

3 Drawing Sheets

Genus and species: *Phalaenopsis* hybrid.
Variety denomination: 'PHA858376'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA858376'.

The new *Phalaenopsis* plant is a product of a planned breeding program conducted by the inventor in Bleiswijk, the Netherlands. The objective of this breeding program was to create a new *Phalaenopsis* plant with attractive, small, light reddish-purple flowers with reddish-purple stripes, white edges, and red-purple lips, suitable for potted plant production.

The new *Phalaenopsis* plant 'PHA858376' is a result of cross-pollination made by the inventor in August 2012 in Bleiswijk, the Netherlands, of the proprietary female, or seed parent, *Phalaenopsis* hybrid '07-000001-3358' (unpatented) with the proprietary male, or pollen parent, *Phalaenopsis* hybrid '07-000001-1898' (unpatented).

The new *Phalaenopsis* was selected by the inventor as a single plant within the progeny of the stated cross-pollination in a controlled greenhouse in Bleiswijk, the Netherlands, in June 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 15, 2021 (Application no. 2021/2265), by Applicant who obtained the subject matter disclosed directly from the inventor. 'PHA858376' has not been made publicly available or sold anywhere in the world prior to the effective filing date of this application with the exception of sales or disclosures made one year or less before the effective filing date of this claimed invention by Applicant who obtained 'PHA858376' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA858376' as a new and distinct variety of *Phalaenopsis* plant:

1) Light reddish-purple flowers with reddish-purple stripes, white edges, and reddish-purple lips;
2) Flower shape in lateral view is flat; and
3) Lip: curvature of lateral lobe is medium.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in October 2022. Colors in the photographs may differ from the color values cited in the detailed botanical description, which accurately describe the actual colors of the new variety.

DESCRIPTION OF THE NEW VARIETY

Figure 1:
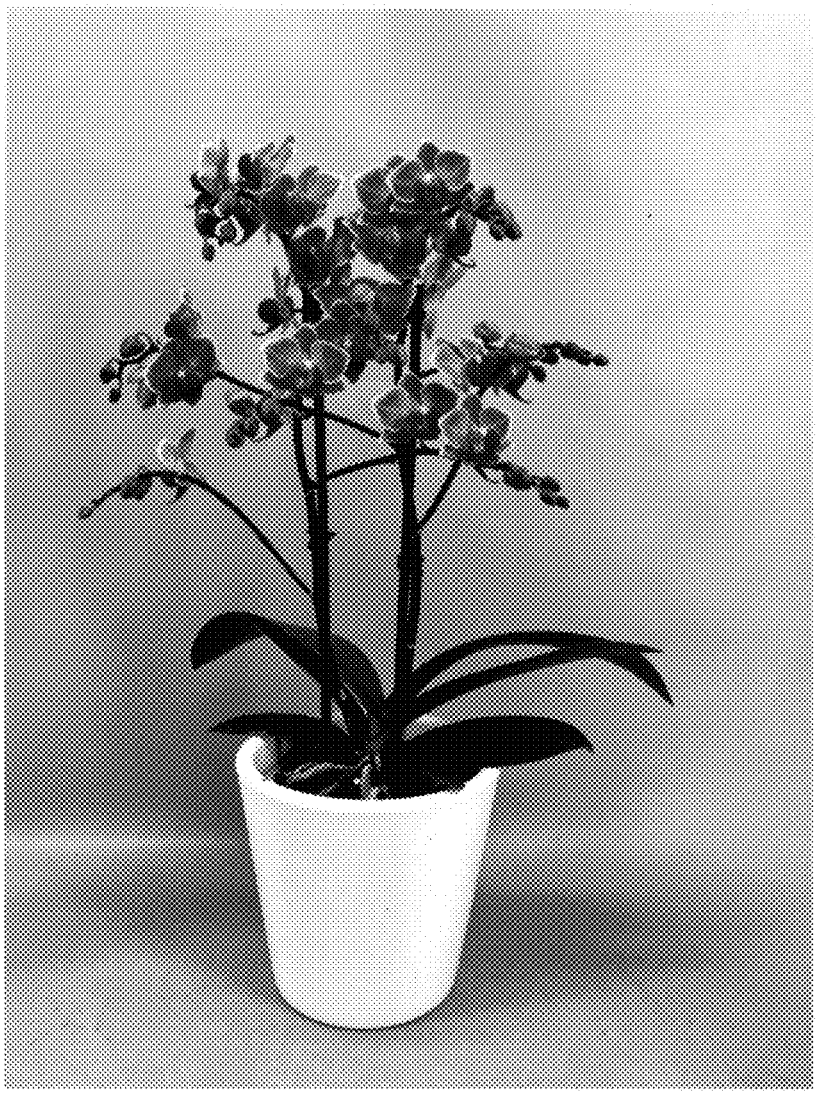
FIG. 1 shows the overall plant habit; including blooms, buds, and foliage of 'PHA858376'.
Figure 2:
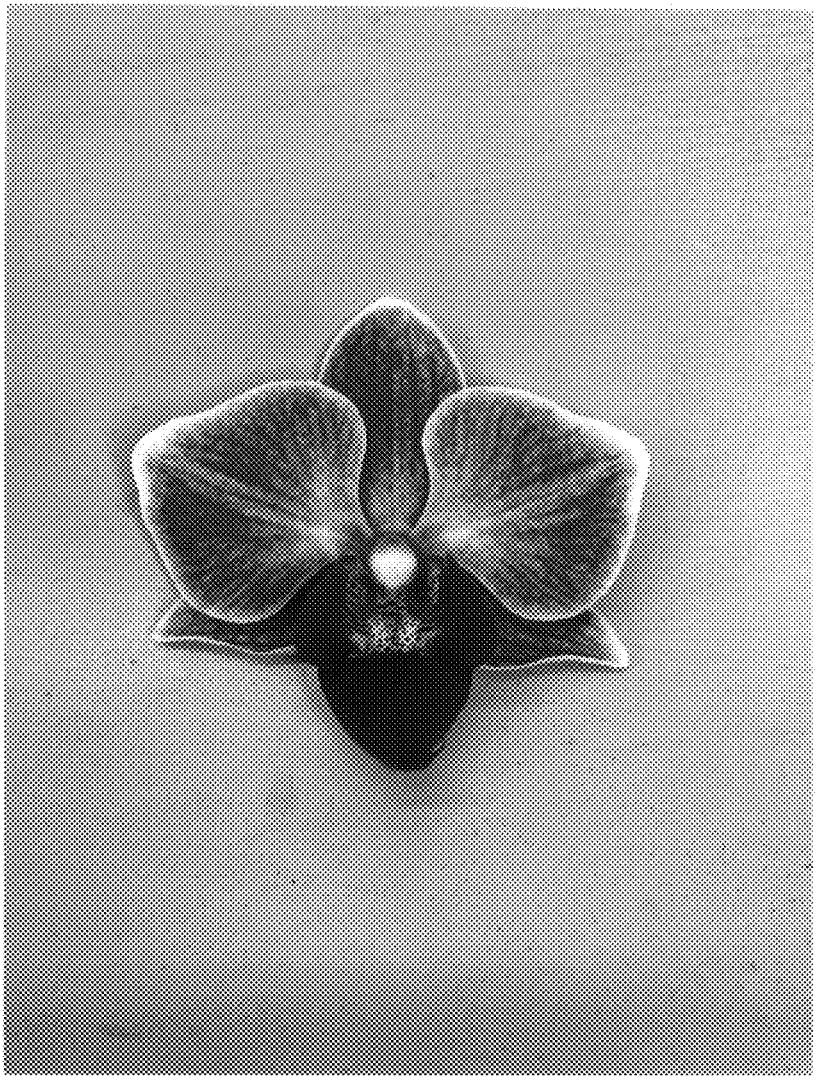
FIG. 2 shows a close-up of a flower of 'PHA858376'.
Figure 3:
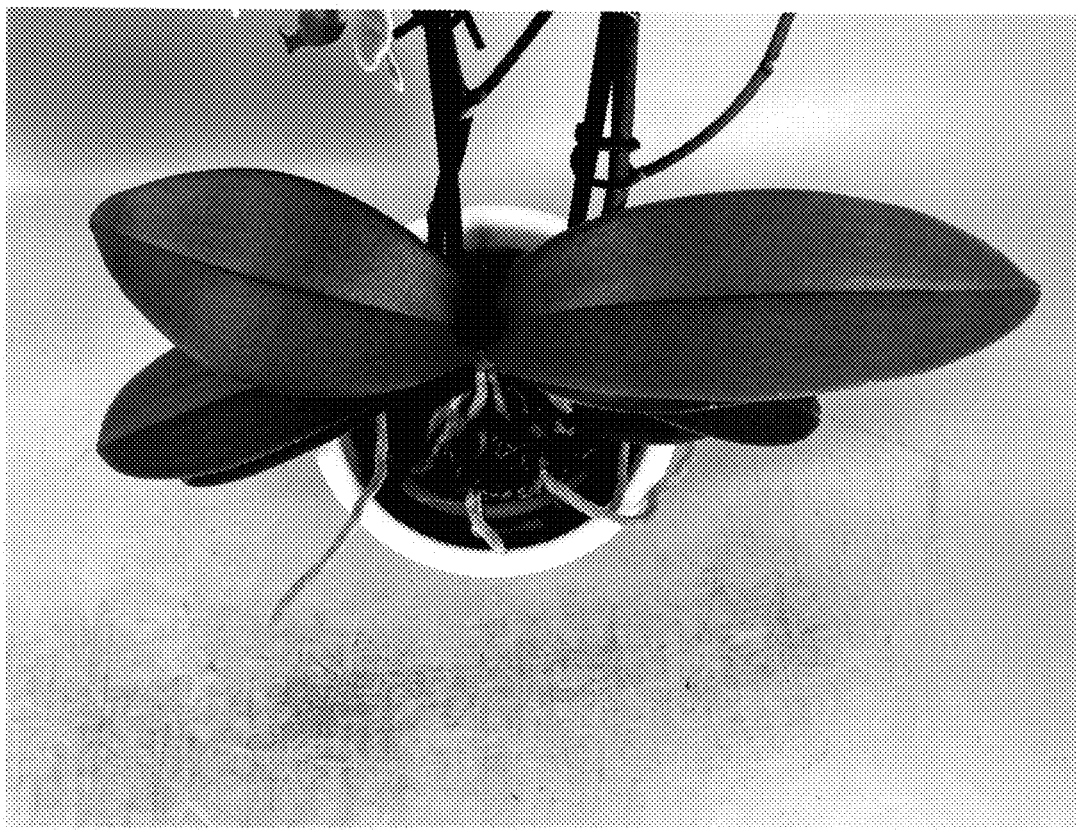
FIG. 3 shows an overhead view of the leaves of 'PHA858376'.

The following detailed description sets forth the distinctive characteristics of 'PHA858376'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in October 2022 on flowering plants which were planted in 12-centimeter (diameter) pots. After in vitro propagation, the plants were grown in nursery trays for 20 to 24 weeks, followed by transplantation into 12-centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA858376'.

Parentage:

*Female parent*.—*Phalaenopsis* cultivar '07-000001-3358' (unpatented).

*Male parent*.—*Phalaenopsis* cultivar '07-000001-1898' (unpatented).

Propagation:

*Type*.—Meristem tissue culture.

Roots:

*Root description*.—Greyed-green (a color in between RHS 190B and RHS 190C) colored roots with branching lateral roots having purplish-red (RHS N77B) colored root tips.

Plant:

*Crop time to flowering*.—Following asexual propagation (in vitro), the rooted cuttings grow for 20 to 24 weeks. After transplantation into 12-cm pots, the plant is finished after 48 to 50 weeks.

*Growth habit of the peduncle*.—Upright to slightly pendent with panicle inflorescence.

*Height* (*from soil level to top of inflorescence*).—Approximately 33.0 cm to 38.0 cm.

*Width* (*measured from leaf tips*).—About 33.0 cm to 35.0 cm.

*Vigor*.—Strong.

Leaves:

*Mature leaves*.—Quantity per plant: 9 to 10 leaves are produced before flowering. Length (fully expanded): 18.0 cm to 20.0 cm. Width: 5.5 cm to 6.5 cm. Position of the broadest part of the leaf: At middle. Shape: Oblong. Base shape: Moderately elongated. Apex: Acute asymmetric. Leaf blade angle with the petiole (measured from the horizontal position): Between 15 degrees and 30 degrees. Leaf margin: Entire. Color: Upper, surface: Green (RHS 146A). Lower surface: Yellow-green (RHS 146B). Texture (both upper and lower surfaces): Smooth. Thickness: 2.0 mm to 3.0 mm. Variegation: Absent. Venation: Pattern: Parallel. Color of the midvein: Upper surface: Green (RHS 146A). Lower surface: Yellow-green (RHS 146B).

Peduncle:

*Quantity per plant*.—1 to 2.

*Number of flowers per peduncle*.—31 to 38.

*Length*.—33.0 cm to 38.0 cm.

*Diameter*.—5.0 mm to 6.0 mm.

*Strength*.—Strong.

*Aspect*.—Upright to slightly pendent.

*Texture*.—Smooth.

*Color*.—Mix of brown (RHS N200A) and green (RHS 146B).

*Internode length*.—1.0 cm to 2.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 2.

*Inflorescence size*.—Height (from base to tip): 200.0 mm to 250.0 mm.

*Flowering time*.—First flowers can be expected 10 to 11 months after planting in a 12-cm pot.

*Flower*.—Height: 36.0 mm to 38.0 mm. Diameter: 48.0 mm to 53.0 mm. Depth of lip: 16.0 mm to 19.0 mm.

*Flower shape*.—Flat.

*Flower longevity*.—On the plant: 8 to 10 weeks.

*Fragrance*.—Absent.

*Flower bud*.—Average size: Medium. Length: 16.0 mm to 18.0 mm. Width: 14.0 mm to 16.0 mm. Shape: Egg shaped. Color: Yellow-green (RHS 145B) with purplish-red shade (RHS N77B) and diluting dark purplish-red stripes (RHS N79C).

*Petals*.—Arrangement: Open/free. Shape: Deltoid. Apex: Obtuse asymmetric. Margin: Moderately undulated. Length (from base to tip): 24.0 mm to 26.0 mm. Width: 24.0 mm to 26.0 mm. Position of the broadest part of the petal: Toward the base. Color (when fully opened): Upper surface: Basic color: Light reddish-purple (RHS N78D). Over color: Reddish-purple stripes (RHS N78B); small white edges (RHS NN155C). Lower surface: Basic color: Very light purple (RHS 76B). Over color: Light reddish-purple stripes (RHS N78D). Number of spots and stripes on the petals (upper surface): Many. Color of spots and stripes on the petals (upper surface): RHS N78B. Density of netting of the petals (upper surface): None. Color of the netting (upper surface): Not applicable.

*Dorsal sepal*.—Shape: Elliptic. Apex: Obtuse symmetric. Margin: Entire. Length (from base to tip): 24.0 mm to 26.0 mm. Width: 26.0 mm to 28.0 mm. Position of the broadest part of the dorsal sepals: At middle. Color (when fully opened): Upper surface: Basic color: Purplish-pink (RHS N78C). Over color: Reddish-purple stripes (RHS N78B) and white edges (RHS NN155C). Lower surface: Basic color: Light purple (RHS 76A). Over color: Purplish-pink (RHS N78C) stripes and small, white (RHS NN155C) edges. Number of spots and stripes on the dorsal sepals (upper surface): Medium stripes. Color of spots and stripes on the dorsal sepals (upper surface):

RHS N78B. Density of netting of the dorsal sepals (upper surface): Low. Color of the netting: RHS N78B.

*Lateral sepals*.—Shape: Ovate. Apex: Acute asymmetric. Margin: Moderately undulated. Length (from base to tip): 25.0 mm to 27.0 mm. Width: 15.0 mm to 17.0 mm. Position of the broadest part of the lateral sepals: Toward the base. Color (when fully opened): Upper surface: Basic color: Purplish-pink (RHS N78C). Over color: Light yellow-green (RHS 145C), dotted RHS 71A at the base; reddish-purple stripes (RHS N78B); small, white edges (RHS NN155C). Lower surface: Basic color: Light purple (RHS 76B). Over color: Touch of light yellow-green (RHS 145C) at the base; purplish-pink stripes (RHS N78C) and reddish-purple midvein (RHS N78B). Number of spots and stripes on the lateral sepals (upper surface): Medium stripes. Color of spots and stripes on the lateral sepals (upper surface): RHS N78B. Density of netting of the lateral sepals (upper surface): Low. Color of the netting (upper surface): RHS N78B.

*Labellum* (*lip*).—Whiskers: Present. Length of whiskers: 5.0 mm to 7.0 mm. Color of whiskers: Reddish-purple (RHS N78A) with purplish-red tips (RHS 71A). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Weakly undulated. Length: 15.0 mm to 17.0 mm. Width: 10.0 mm to 12.0 mm. Color: Upper surface: Light yellow-green (RHS 155A) and striped at the base RHS 59A; purplish-red (RHS 59B) and reddish-purple (RHS N78A) toward the tips. Lower surface: White (RHS 155C) at the base; dark red-purple on one side (a color in between RHS 59A and RHS N186D) and reddish-purple (RHS N78A) toward the other side and tips. Number of spots and stripes on the lateral lobe: Few stripes. Color of spots and stripes on the lateral lobe: RHS 59A. Density of netting of the lateral lobe: None. Color of the netting: Not applicable.

*Apical lobe*.—Shape: Ovate. Margin: Entire. Length: 17.0 mm to 19.0 mm. Width: 15.0 mm to 17.0 mm. Color: Upper surface: Touch of yellow (RHS 13A) margin at the base of apical lobe; dark red-purple at the base (a color in between RHS N186D and RHS 187C); reddish-purple (a color in between RHS N78A and RHS N79C) toward the whiskers. Lower surface: White (RHS NN155C) at the middle from base toward whiskers; purplish-red wings (RHS 59B); reddish-purple (RHS N78A) towards margins and tips. Number of spots and stripes on the apical lobe: None. Color of spots and stripes on the apical lobe: Not applicable. Density of netting of the apical lobe: None. Color of the netting: Not applicable. Bump and ride: Absent.

*Callus*.—Average size: Small. Height: 4.0 mm to 5.0 mm. Length: 4.0 mm to 5.0 mm. Width: 3.0 mm to 4.0 mm. Color: Light yellow-green (RHS 155A); light yellow-green (RHS 4D) toward tips; dotted RHS N79C.

Reproductive organs:

*Column*.—Length: 8.0 mm to 9.0 mm. Diameter: 4.0 mm to 5.0 mm. Color: Purplish-pink (RHS N78C) with a touch of reddish-purple (RHS N78B) toward the tips.

*Pollinia*.—Quantity: 2. Diameter: 0.9 mm to 1.1 mm. Color: Orange-yellow (RHS 23A).

*Ovary*.—Length: 10.0 mm to 12.0 mm. Diameter: 1.7 mm to 2.0 mm.

*Pedicel*.—Length: 27.0 mm to 29.0 mm. Diameter: 2.1 mm to 2.4 mm. Color: Yellow-green (RHS 146D) at the base; light yellow-green (RHS 145C) with a touch of very light purple (RHS 76B) toward the flowers. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA858376' differs from the female parent plant '07-000001-3358' (unpatented) in that 'PHA858376' has deltoid shaped petals, flowers that are flat in lateral view, and reddish-purple whiskers with purplish-red tips, whereas '07-000001-3358' has moderately compressed to medium shaped petals, flowers that are concave in lateral view, and reddish-purple whiskers with white tips.

'PHA858376' differs from the male parent plant '07-000001-1898' (unpatented) in that 'PHA858376' has reddish-purple whiskers with purplish-red tips and absent of spots on the apical lobe, whereas '07-000001-1898' has very light purple whiskers with light orange-yellow tips and a medium number of spots on the apical lobe.

'PHA858376' is most similar to the commercial *Phalaenopsis* plants named 'PHALFAUF' (U.S. Plant Pat. No. 30,992) and 'PHALFATYMO' (U.S. Plant Pat. No. 32,478). 'PHA858376' differs from the commercial variety 'PHALFAUF' in that 'PHA858376' has light reddish-purple petals on the upper side, light yellow-green callus, and semi-erect to horizontal leaf attitude, whereas 'PHALFAUF' has very light purple petals on the upper side, yellow callus, and horizontal to semi-drooping leaf attitude. Additionally, the leaf length of 'PHA858376' is longer than 'PHALFAUF'.

'PHA858376' differs from the commercial variety 'PHALFATYMO' in that 'PHA858376' has flat flowers in lateral view, semi-erect to horizontal leaf attitude, and ovate lips of apical lobe, whereas 'PHALFATYMO' has concave flowers in lateral view, semi-drooping leaf attitude, and elliptic lips of apical lobe.

I claim:

1. A new and distinct variety of *Phalaenopsis* plant named 'PHA858376', substantially as described and illustrated herein.

* * * * *